United States Patent [19]

Yanong

[11] 4,429,689
[45] Feb. 7, 1984

[54] SEX AID DEVICE FOR MALES

[76] Inventor: Procopio U. Yanong, 1900 Half Day Rd., Bannockburn, Ill. 60015

[21] Appl. No.: 382,253

[22] Filed: May 26, 1982

[51] Int. Cl.³ .............................................. A61F 5/42
[52] U.S. Cl. ..................................................... 128/79
[58] Field of Search ............................................ 128/79

[56] References Cited

U.S. PATENT DOCUMENTS

| 1,270,880 | 7/1918 | Scheinkman | 128/79 |
| 1,511,572 | 10/1924 | Marshall | 128/79 |
| 2,899,957 | 8/1959 | Briggs | 128/79 |
| 3,495,588 | 2/1970 | Walters | 128/79 |
| 4,022,196 | 5/1977 | Clinton | 128/79 |

Primary Examiner—Dalton L. Truluck
Attorney, Agent, or Firm—Richard G. Kinney

[57] ABSTRACT

A sex aid device for males is disclosed comprising a tubular member that includes upper and lower longitudinally extending relatively inelastic but flexible supports and connecting elastic flexible sides, said tubular member being adapted to extend from the base of a penis to the glans penis, and the bottom support extending forward and forming a relatively inelastic spoonlike member for receiving the bottom of the glans penis to be exposed to tactile stimulation, said spoonlike member having a forward-extending smooth tip of soft compressible elastic material formed thereon. The device further preferably has upper and lower transverse ridges of smooth-surfaced compressible elastic material at the upper and lower lengths of the tubular member and one or two transverse side slits intermediate the length of the tubular member to aid in insertion of a non-erect penis. A pair of tapes is preferably secured to the upper portion of the tubular member at the base end, and a tape is attached at the bottom thereof to aid in attaching the device about the body of the user.

9 Claims, 8 Drawing Figures

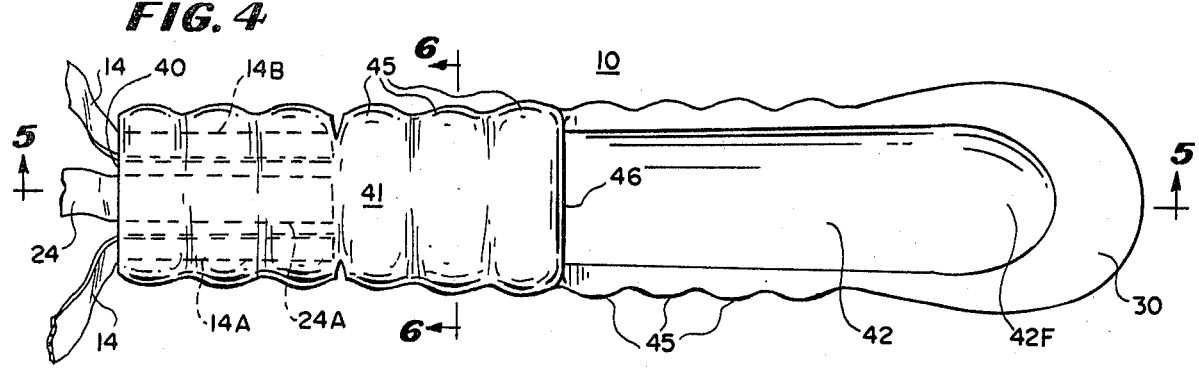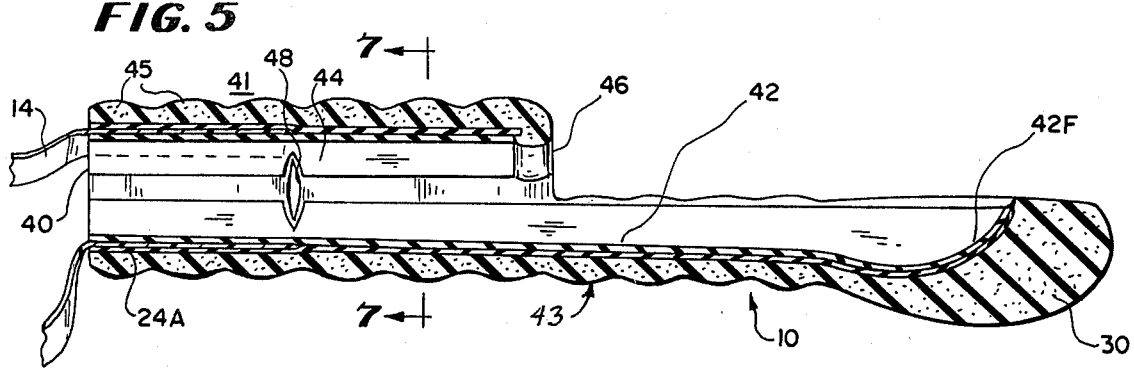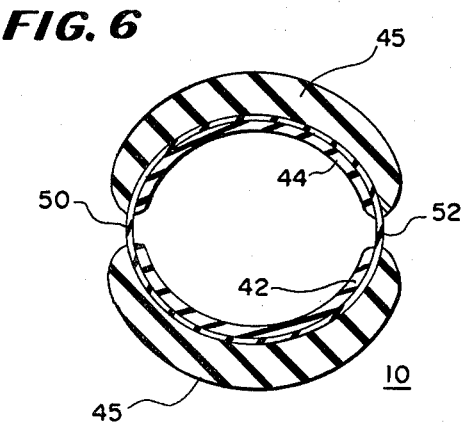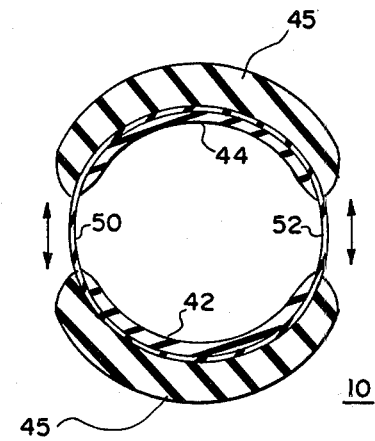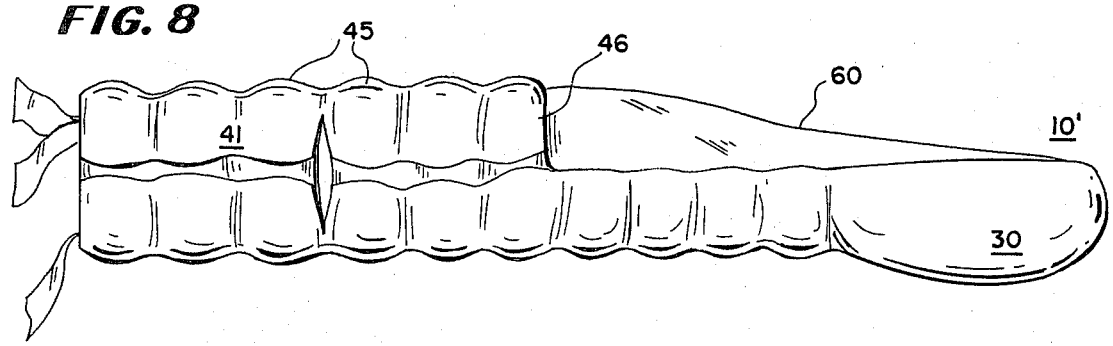

SEX AID DEVICE FOR MALES

FIELD OF THE INVENTION

The present invention is directed to an improved device for attachment and use with a penis to aid in the act of sexual intercourse.

BACKGROUND OF THE INVENTION

A number of devices have been proposed in the past for treating impotence or for serving as a prosthetic penis. U.S. Pat. Nos. 837,993; 1,216,099; 1,362,398; 3,131,691; 3,495,588; 3,939,827; 4,022,196; 4,206,752; and 4,262,662 illustrate a variety of approaches to this problem over the past three-quarters of a century.

SUMMARY OF THE PRESENT INVENTION

The present invention provides a sex aid device comprising a generally tubular member adapted to receive a penis, which tubular member includes a relatively inelastic but flexible longitudinal support, and is transversely elastic so as to receive in a close fit an unerect penis and to expand transversely to allow for the swelling of a penis during erection. The tubular member is adapted to extend from the base of the penis to the glans penis. A spoonlike member of inelastic but flexible material is formed unitarily with said tubular member and adapted to receive the bottom of the glans penis while allowing the upper surface thereof to be free to receive tactile stimulation, said spoonlike member having a forward-extending smooth tip of soft compressible elastic material.

This construction provides the device with the advantages of a prosthesis, but also serves as a splint since it allows the upper portion of the glans penis to be tactilely stimulated. Thus the device can be used by those who suffer from complete impotence, as in the case of physical damage, and also those who suffer from periodic or partial impotence, in which case it aids in achieving and accommodating an erection.

The invention, together with the advantages thereof, may best be understood by reference to the following description taken in connection with the accompanying drawings, in the several figures of which like reference numerals identify like elements.

BRIEF DESCRIPTION OF THE DRAWINGS

FIG. 4 is a top view of the device of FIGS. 1 through 3 with some internal parts shown in dashed outline.

FIG. 5 is a longitudinal vertical sectional view of the device of FIGS. 1 through 3 in moved position, as seen from the plane indicated by the line 5—5 of FIG. 4 as seen looking in the direction of the arrows.

FIG. 6 is a vertical, cross-sectional view of the device of FIGS. 1 through 5 as seen when looking in the direction of the arrows, from the plane defined by the line 6—6 of FIG. 4.

FIG. 7 is a cross-sectional view, similar to that of FIG. 5, showing the device expanded as seen from the plane defined by the line 7—7 of FIG. 5.

FIG. 8 is a side view similar to that of FIG. 3 of a second embodiment of the present invention.

DETAILED DESCRIPTION OF THE DRAWINGS

Figure 1:
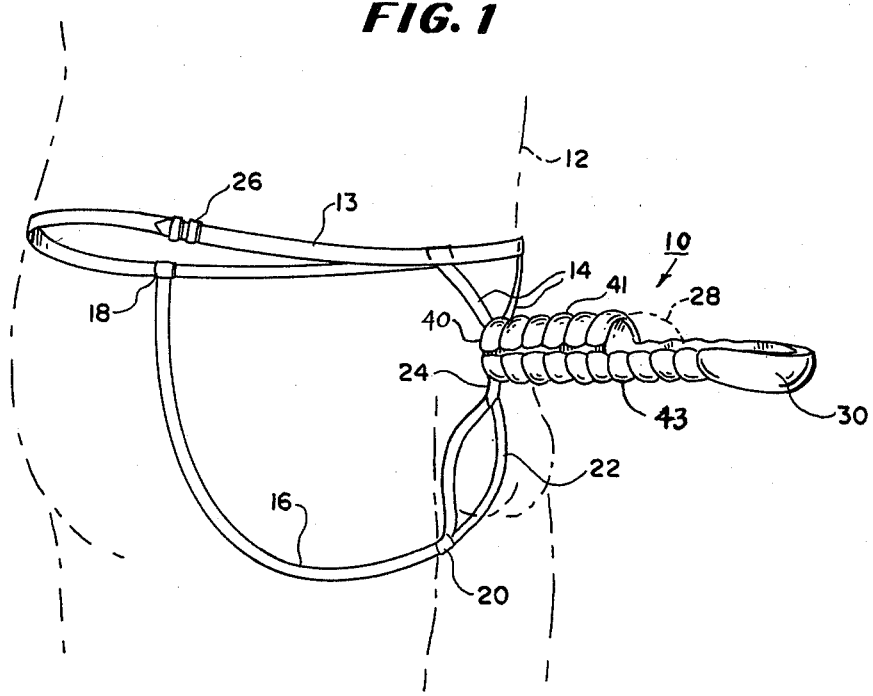
FIG. 1 is a perspective view of a sex aid device constructed in accordance with the present invention on a male human, shown in phantom lines, illustrating the method of use and attachment to the user.

Referring to FIG. 1, there is a depicted a device constructed in accordance with the principles of the present invention and generally designated by the number 10. The device 10 is shown on a male patient 12, shown in phantom lines, and is secured to the user 12 by means of a harness which includes a belt 13 which encircles his waist just above the hips. A pair of straps or tape segments 14 are secured to the device 10 and to spread-apart points on the front of the belt 13. A strap 16 is attached to the back of the belt 13 at point 18, and passes between the legs of the user. At a point 20 on strap 16, just below the scrotum, the strap 16 is formed in two segments to form a loop 22 for surrounding the scrotum. This loop 22 is closed to again reform a single strap segment 24 above the scrotum. The two tape segments 14 and segment 24 are secured to the device 10 at its base 40, preferably in a manner that will be explained below in connection with FIGS. 3 through 5.

The belt 13 is preferably a small belt, custom fit to a convenient length and adjustably connected to a buckle 26, just like a conventional belt and buckle, except that it must be very small and strong so as not to be bulky. The two harnesses 14 in front will be attached to the belt 13 at two points of the belt in front. Strap 16 is attached to the belt 13 at point 18 at the back of the user.

For ease of use, the harness is preferrably releasably secured in front to the belt 14 which is adjustably connected by a conventional and conveniently located buckle 26.

As shown in FIG. 1, the device 10 is formed so as to receive and surround the unerect penis of the user 12, and, in accordance with the present invention, with the dorsal portion of the glans penis 28 exposed to tactile stimulation and with an artificial glans penis 30 formed on a longitudinal extension of the device 10.

The device 10 comprises a generally tubular member 41 adapted to receive the penis within it. The tubular member 41 is adapted to extend from the base of the penis to terminate dorsally just behind the glans penis 28 and has a ventral portion 43 that terminates with artificial glans penis 30.

The device 10 is formed to be flexible but generally inelastic in length, with the artificial glans penis formed of soft compressible material. It is also preferably formed with ribs 45, also of soft compressible material. The outer soft cover need not be ribbed as long as it is soft compressible or foam material.

Figure 2:
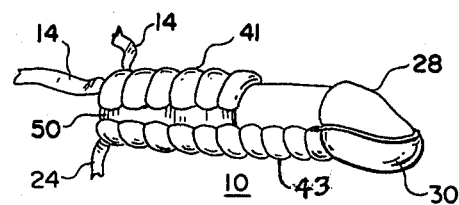
FIG. 2 is a perspective view similar to that of FIG. 1, further illustrating the device in use.

The dorsal portion of the glans penis is exposed to tactile stimulation and the device is constructed to accommodate the erection of the penis by being able to expand in its effective diameter, as well as to allow the extension of the penis, as shown in FIG. 2. The device 10 is preferably sized to the individual user to allow for a full erection (when such is medically possible) within the spoonlike member formed to receive the penis. However, if the erect penis should extend further, the device readily adapts to this with the natural glans penis advancing over the artificial glans penis 30 and bending it downward slightly.

Figure 3:
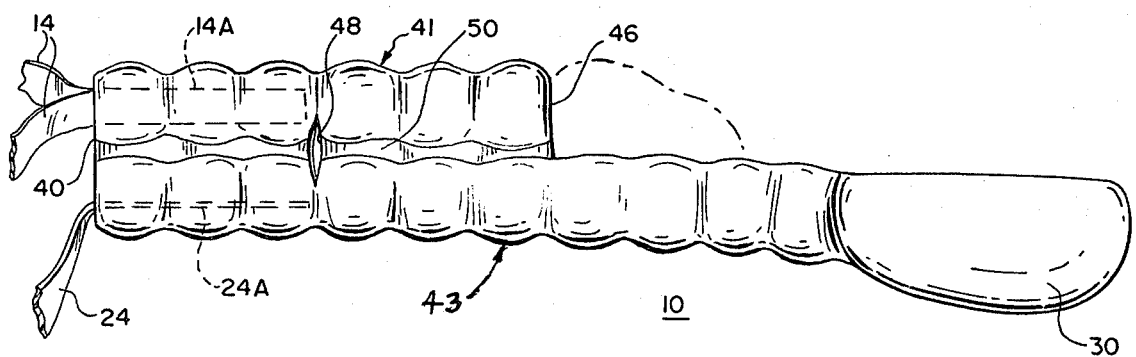
FIG. 3 is a side view of the device of FIGS. 1 and 2 in use on a penis with the glans penis shown in phantom outline and some internal parts shown in dashed outline.

The construction of the device 10 can be seen in more detail in FIGS. 3 through 5. Referring to these figures, it can be appreciated that the device 10 is constructed with a longitudinally extending ventral support 42 which extends from the base 40 of the device to the artificial glans penis 30. The support 42 is of concave troughlike shape to conform to and receive the ventral portion of the penis, and forms a forward spoonlike member 42F as best seen in FIGS. 4 and 5. This support 42 and extension member 42F are formed of a relatively inelastic but flexible material, for example a latex compound such as those used in catheters.

A second upper or dorsal support member 44 of similar material and properties as the member 42 is provided to extend along the dorsal portion of the device and extend from the base 40 to the surface, designated 46, of the tubular member. This member 44 is also shaped to conform to penis shape and is concave downward, as better seen in FIG. 6.

Spanning the supports 42 and 44 and completing the tubular member are elastic webs 50 and 52. These are preferably formed of elastic latex such as that used in surgical or examining gloves or prophylactics. As indicated in FIGS. 5 and 6, these webs are preferably formed by forming a layer completely around the outside of the supports 42 and 44 as, for example, by dipping into a latex solution prior to curing.

The tape segments 14 and 24 are preferably made of nylon belting, e.g., 3/8 inch wide woven nylon tape, and secured to the device 10 by having the tape segment 14 ends 14A and 14B and strap 24A longitudinally embedded in the device 10 and emerging therefrom at its base 40. This is done by sandwiching the tape segments 24A, 14A, and 14B between layers of material of the device.

The transverse extending ribs 45 are formed about both the dorsal and ventral support members 42 and 44 (with the web material sandwiched between them), preferably to approximately meet as shown in FIG. 3. These ribs are preferably formed of sponge latex formed by the application of latex formula containing a blowing agent to the outer surface of the support 42, 42F, and 44, and by curing the unit in a cavity mold that determines the shape of the ribs and artificial glans 30 substantially as shown, and which will produce a smooth outer surface thereon.

As shown in FIG. 5, the surface 46 is preferably formed with a rib that extends within the tubular opening formed for receiving the penis and serves to hold the natural glans penis in place after its insertion.

To aid in inserting the penis, one or a pair of transverse slits 48 may be formed in the tubular elastic sections 50 and 52 to allow one's fingers to enter the unit at those points.

As indicated in FIGS. 5, 6, and 7, the webs 50 and 52 are elastic and can stretch to increase the transverse internal area of the tubular segment of the device 10 so as to accommodate expansion of the penis.

The device 10 is preferably made by first forming the supports 42 and 44 on a mandrel, then placing the tape segments 14A, 14B and 24 in place, and dipping the mandrel and supports into latex formula to form the webs 50, 52, applying a latex formula containing a blowing agent to the outside of the unit and curing the unit in a cavity mold, wherein the blowing agent would extend the latex to form the ribs 45 and artificial glans 30. Thereafter, the device is cooled, removed, trimmed, and the slits 48 made.

This method of manufacture lends itself easily to forming an alternative device 10' depicted in FIG. 8, wherein prophylactic protection is provided. This device 10' is essentially similar to that of FIGS. 1 through 7, except for the addition of a thin elastic cover or shield 60 which covers and encloses the area from rib 46 to the forward spoonlike member 42F.

This shield 60 may be easily formed unitarily and at the same time with the webs 50, 52, by dipping the mandrel carrying the supports 42, 44, entirely into a liquid latex solution in a manner similar to that used in making surgical gloves. Of course, a conventional prophylactic shield could be used in addition to the device 10 of FIGS. 1 through 7.

It should be noted that although the supports 42 and 44 and web material 50, 52, and optional shield 60, and the ribs 45 and glans 30 material are depicted as separate layers, they are preferably bonded together and cured together so as to form a unitary structure. Since the preferred material for making these parts or layers is latex (of differing formulations) they will weld or melt together easily and indeed the dividing line between them will naturally blend so that the transfer from relatively inelastic structural latex to elastic and formed latex will be more gradual than shown. Although preferably of all latex construction, part or all of the device may be formed of other materials, e.g., vinyl may be substituted for the support members if desired.

The device will, in most cases, be proportioned to the patient's physical requirements. In most cases, the tubular member will be constructed with approximately one inch inside diameter, a length of two to four inches from the base 40 to the rib 46, and an overall length of about $6\frac{1}{2}$ to 7 inches.

OPERATION

In use, the user 12 would first apply the device 10. The penis would be drawn through the tubular portion of the device (using the slits 48 if necessary) so that the glans penis would be positioned at last as shown in FIGS. 1 and 3. The user would then attach the harness, including the belt 13 and strap 14 and 16 as shown in FIG. 1. In this arrangement, the user may engage in sexual intercourse. The length of the device 10 is such as to approximate the erect penis and the artificial glans 30 and serves to provide the user's partner with a simulated erect penis.

The exposure of at least the dorsal portion of the glans penis to tactile stimulation (either directly or through the thin prophylactic shield 60) provides the user with much of the same stimulus and feeling he would obtain if he had an erection and was engaging in normal sexual intercourse. Should he be able to achieve erection, the device 10 expands as shown in FIGS. 5 and 7 with the webbing 50 and 52 stretching and the natural glans penis traveling down the trough formed by support member 42 to the spoonlike member 42F to the approximate position of the artificial glans penis, and intercourse may continue uninterrupted and without any need to remove the device.

It should be noted that the device can be used to continue sexual intercourse, if desired, after the user's erection has passed, as from premature ejaculation. This allows the male user to more completely fulfill his role and to satisfy his partner. This aspect of the device may lead to its use in treating sexual problems other than impotence.

While two particular embodiments of the invention have been shown and described, it will be obvious to those skilled in the art that changes and modifications may be made without departing from the invention in its broader aspects and, therefore, the aim in the appended claims is to cover all such changes and modifications and fall within the true spirit and scope of the invention.

I claim:

1. A sex aid device for use with a penis, comprising a generally tubular member adapted to receive a penis, said tubular member being adapted to extend from the base of and terminate dorsally just behind the glans penis of an unerect penis, and which tubular member includes at least one relatively inelastic but flexible longitudinally extending support member which extends from the base to the tip of the penis ventrally to receive the ventral portion of the glans penis while allowing the dorsal portion thereof to be free to receive tactile stimulation; said support member having a spoonlike forward extension member and having a forward-projecting tip of soft compressible elastic material affixed to said extension member and shaped to form an artificial glans penis.

2. The sex aid device as defined in claim 1, wherein said tubular member forms an closed loop of material about the penis and is transversely elastic so as to receive in a close fit an unerect penis, but to elastically expand transversely to allow for the swelling of a received penis.

3. A sex aid device for use with a penis, comprising a generally tubular member adapted to receive a penis, said tubular member being adapted to extend from the base of and terminate dorsally just behind the glans penis of an unerect penis, and which tubular member includes at least one relatively inelastic but flexible longitudinally extending support member which extends from the base to the tip of the penis while allowing the dorsal portion thereof to be free to receive tactile stimulation; said support member having a spoonlike forward extension member and having a forward-projecting tip of soft compressible elastic material shaped to form an artificial glans penis, wherein said tubular member is transversely elastic so as to receive in a close fit an unerect penis, but to elastically expand transversely to allow for the swelling of a received penis, and wherein the tubular member longitudinally extending support extends along the bottom of the tubular member and a second longitudinally extending support extends along the top of the tubular member, each of said supports being shaped to conform to the walls of the tubular member, and said tubular member includes elastic sidewall sections spanning the longitudinal support members and providing the transverse elasticity to the tubular member.

4. The device of claim 3 wherein smooth-surfaced transverse ribs of soft, resiliently compressible material are formed at the top and bottom surfaces of said tubular member.

5. The device of claim 4 which is formed unitarily of latex with the longitudinal supports and spoonlike member being formed or relatively inelastic, relatively thick latex, and having said sidewalls formed of thin elastic latex, and the soft, resiliently compressible tip and ridges formed of latex made with a blowing agent to form a sponge-like material.

6. The device of claim 5 wherein means for attaching the device to the body of a user are affixed to the tubular member at the base end thereof.

7. The device of claim 6 wherein the means for attaching include tapes that have ends attached to the member by having a length thereof captivated between layers of the latex forming the supports members and that forming the ridges.

8. The device of claim 3 wherein a thin envelope of loose-fitting elastic material is formed to cover the spoonlike opening and, with the tubular member and spoonlike member, serves to envelope and protect the penis from infection and to prevent ejection of semen through the device during use.

9. The device of claim 1 wherein said tubular member has means (14,24 etc.) for securing it at the base of a natural penis, and said spoonlike forward extension (30) extends forward from the position of the natural glans penis of an unerect penis for a sufficient length to form a trough so as to allow the natural glans penis to travel along trough if the natural penis achieves erection.

* * * * *